United States Patent
Fargahi

(10) Patent No.: US 11,020,562 B2
(45) Date of Patent: Jun. 1, 2021

(54) INSERTION DEVICE FOR INSERTION OF A MEDICAL IMPLANT

(71) Applicant: BIOTRONIK AG, Buelach (CH)

(72) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 562 days.

(21) Appl. No.: 14/741,601

(22) Filed: Jun. 17, 2015

(65) Prior Publication Data

US 2016/0030712 A1 Feb. 4, 2016

Related U.S. Application Data

(60) Provisional application No. 62/030,623, filed on Jul. 30, 2014.

(51) Int. Cl.
*A61B 17/34* (2006.01)
*A61M 25/00* (2006.01)
(Continued)

(52) U.S. Cl.
CPC ..... *A61M 25/0054* (2013.01); *A61B 17/3468* (2013.01); *A61F 2/2436* (2013.01); *A61F 2/966* (2013.01); *A61M 25/005* (2013.01); *A61M 25/0043* (2013.01); *A61M 25/0138* (2013.01); *A61B 17/12136* (2013.01); *A61B 2017/1205* (2013.01); *A61F 2/962* (2013.01); *A61F 2002/9528* (2013.01); *A61F 2002/9534* (2013.01); *A61F 2002/9665* (2013.01)

(58) Field of Classification Search
CPC ........ A61M 2025/1081; A61M 31/007; A61M 37/0069; A61M 31/002; A61M 31/00; A61B 17/3468; A61B 2017/1205; A61F 2/2436; A61F 2/966; A61F 2/962; A61F 2002/9528; A61F 2002/9534; A61F 2002/9665
See application file for complete search history.

(56) References Cited

U.S. PATENT DOCUMENTS

2005/0251102 A1\* 11/2005 Hegland ............... A61M 39/12
604/500
2005/0288764 A1\* 12/2005 Snow ........................ A61F 2/95
623/1.11
(Continued)

FOREIGN PATENT DOCUMENTS

EP 0741022 A2 11/1996
WO WO 2014020565 A1 \* 2/2014 ............. A61B 17/11
WO WO-2014020565 A1 \* 2/2014 ............. A61B 17/11

OTHER PUBLICATIONS

European Search Report dated Dec. 10, 2015.

*Primary Examiner* — William R Carpenter
*Assistant Examiner* — William R Frehe
(74) *Attorney, Agent, or Firm* — Greer, Burns & Crain, Ltd.; Steven P. Fallon

(57) ABSTRACT

An insertion device for the insertion of a medical implant into a human and/or animal body. The device has at least one outer shaft, which has a proximal end and a distal end opposite the proximal end. A receiving element is connected to the outer shaft, for the implant. The outer shaft and the receiving element are surrounded at a transition between the outer shaft and receiving element by a locally placed sleeve, which dampens mechanical tensile and/or compressive stresses.

13 Claims, 2 Drawing Sheets

(51) Int. Cl.
*A61M 25/01* (2006.01)
*A61F 2/24* (2006.01)
*A61F 2/966* (2013.01)
A61F 2/95 (2013.01)
A61B 17/12 (2006.01)
A61F 2/962 (2013.01)

(56) References Cited

U.S. PATENT DOCUMENTS

| | | | |
|---|---|---|---|
| 2007/0078504 A1* | 4/2007 | Mialhe | A61B 17/0057 623/1.11 |
| 2009/0287292 A1* | 11/2009 | Becking | A61F 2/97 623/1.11 |
| 2010/0121270 A1* | 5/2010 | Gunday | A61B 17/22012 604/98.01 |
| 2010/0234876 A1* | 9/2010 | Watson | A61B 18/02 606/194 |
| 2010/0262227 A1 | 10/2010 | Rangwala et al. | |
| 2011/0251660 A1* | 10/2011 | Griswold | A61N 1/37205 607/126 |
| 2012/0101561 A1 | 4/2012 | Porter | |
| 2012/0130468 A1* | 5/2012 | Khosravi | A61F 2/2475 623/1.11 |
| 2013/0060279 A1* | 3/2013 | Yassinzadeh | A61B 17/0057 606/213 |
| 2013/0345561 A1* | 12/2013 | Quigley | A61B 90/39 600/435 |
| 2014/0330219 A1* | 11/2014 | Quint | A61F 2/966 604/264 |

* cited by examiner

INSERTION DEVICE FOR INSERTION OF A MEDICAL IMPLANT

PRIORITY CLAIM

This application claims priority under 35 U.S.C. § 119 from prior U.S. Provisional Application No. 62/030,623, filed Jul. 30, 2014.

FIELD OF THE INVENTION

A field of the invention is insertion devices, in particular catheters, for insertion of a medical implant into a human and/or animal body.

BACKGROUND

Medical implants are often introduced into an animal and/or human body for treatment. Permanent and long-term implants carry out replacement functions. Example implants include heart pacemakers, brain pacemakers for Parkinson's patients, cardiac implants, cochlear implants, retinal implants, dental implants, implants for joint replacement, vessel prostheses, or stents. In the field of cardiac implants, valve implants are known, for example aortic valve implants, which perform the function of the natural aortic valve.

Implants are connected to catheters before insertion into the body and have to be fastened such that they can be placed precisely and released in a defined manner by the catheter at the site of use without causing complications. A frequent problem concerns positioning the implant at a defined position. If the implant is placed in an incorrect position, this may lead to a failure of the implant. This often occurs for example with calcification, i.e., the deposit of calcium salts, in particular calcium phosphate (hydroxyapatite), on the structures of the heart and in particular with highly asymmetrically calcified aortic stenosis. It is therefore often the case that the released implant can be withdrawn again completely or in part into the insertion device and either removed or released again at another location. With a catheter length of a meter and more, this constitutes a mechanical load for the insertion device, and in addition the insertion device has to allow curving and bending along its longitudinal extension.

SUMMARY OF THE INVENTION

An insertion device for inserting a medical implant into a human and/or animal body is provided by a preferred embodiment of the invention. The insertion device has at least one outer shaft having a proximal end and a distal end opposite the proximal end. The distal end has a receiving element, which is connected to the outer shaft, for the implant. The outer shaft and the receiving element are surrounded at a transition between the outer shaft and receiving element by a locally placed sleeve. The locally placed sleeve dampens mechanical tensile and/or compressive stresses. The sleeve preferably covers at least a proximal end of the receiving element. The sleeve is preferably formed of a material that can be contracted selectively from a state that is widened based on an inner diameter of the sleeve into a shrunken state. Preferred materials include thermoplastics that contract when heated. Other embodiments include materials that contract without needing to be heated, known as cold-shrink materials. A particular preferred material is PEEK (polyether ether ketone). The sleeve preferably has slits, which are preferably arranged at the transition between the outer shaft and receiving element. The receiving element is preferably configured to release and/or withdraw a self-expanding stent system.

BRIEF DESCRIPTION OF THE DRAWINGS

The invention is explained in greater detail hereinafter by way of example on the basis of exemplary embodiments illustrated in drawings, in which.

DETAILED DESCRIPTION OF THE PREFERRED EMBODIMENTS

Figure 1:
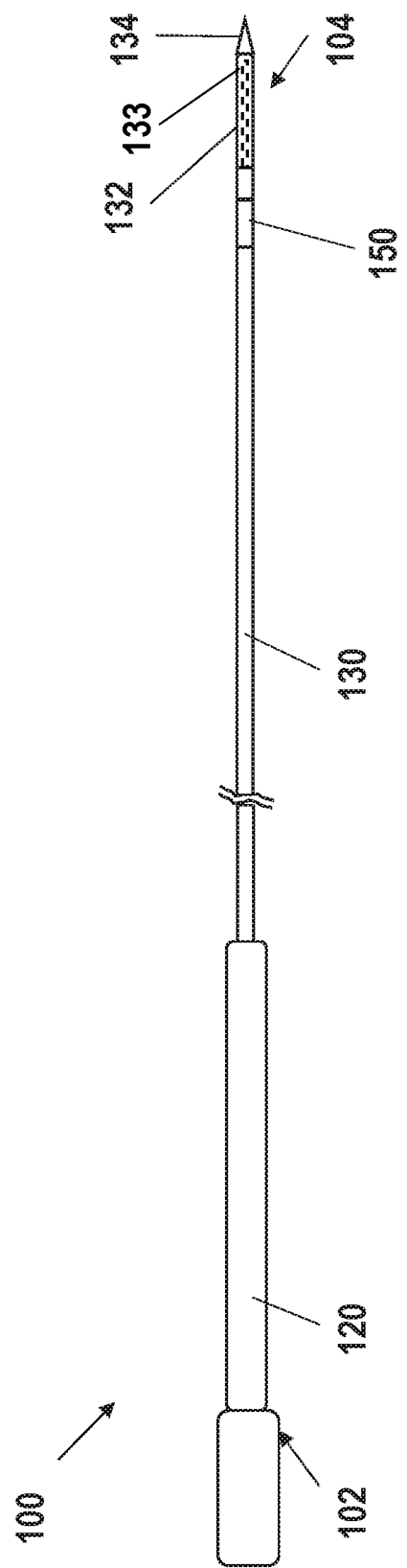
FIG. 1 schematically shows a view of an insertion device in accordance with an exemplary embodiment of the invention, in the form of a catheter with a capsule as receiving element for an implant.

Insertion devices of the invention provide for a reliable release of a medical implant and, where necessary, a reliable retraction of the implant into the insertion device. The sleeve that surrounds the outer shaft and the receiving element at a transition between the outer shaft and receiving element advantageously stabilizes the region of the insertion device, which in particular is exposed to strong tensile and/or compressive stresses during use. In a preferred intended use, the outer shaft is the outer delimitation of the insertion device and can surround one or more inner shafts. The outer shaft of the insertion device is flexible in order to bring the implant to its intended location in the body. The catheter loads in the curved state generate mechanical stresses. If these stresses are damped, a deformation or a kinking of the outer shaft can be avoided.

The insertion device according to the invention allows a reliable release of the implant from the insertion device. Typically, the receiving element, a capsule or the like, in which the implant is guided to its intended location, is arranged at the distal end of the insertion device. Insertion devices such as catheters have lengths of more than a meter, and therefore there is a kink risk at the distal end. A kink in the shaft, in particular in the outer shaft of the insertion device, can impair the release of the implant or even make this impossible. A withdrawal of the implant into the receiving element can also be impaired or made impossible.

The locally placed sleeve at the distal outer shaft allows a reliable release of the implant from the receiving element and, where necessary, a reliable withdrawal of the implant into the receiving element.

The insertion device according to the invention is particularly favorable in the case of the release of self-expanding stent systems, for the withdrawal of the protection of balloon-expanding stents or for the withdrawal of the protection of coated balloons. The design is easy to implement and is cost-effective.

In accordance with a preferred embodiment, the sleeve can cover at least a proximal end of the receiving element. The receiving element is typically fixedly connected to the outer shaft, for example adhesively bonded. This region of the insertion device is at particular risk of kinking.

In accordance with a preferred embodiment, the sleeve can be formed from a material that, based on its inner diameter, can be selectively contracted from a widened state into a shrunken state. In particular, the sleeve can be formed from a thermoplastic which contracts under the action of heat. The use of PEEK (polyether ether ketone) is advantageous. A material that also contracts without the action of heat is utilized in other embodiments, such as what is known as a cold-shrink tubing made of EDPM (ethylene propylene diene monomer, ethylene propylene diene rubber) or silicone.

In accordance with a preferred embodiment, the sleeve may have at least one first and one second region, wherein the first region is arranged toward the proximal end of the insertion device at the transition between the outer shaft and receiving element and is shrunk, and the second region is arranged toward the distal end over the receiving element and is less shrunk than the first region. The floating mounting over the receiving element allows a particularly supporting effect of the sleeve at the transition between the outer shaft and receiving element. In particular, a sufficient movability of the receiving element is ensured.

In accordance with a preferred embodiment, the sleeve may have slits. The flexibility of the sleeve, particularly in the shrunken state, can thus be influenced. Advantageously, the slits can be arranged at the transition between the outer shaft and receiving element, such that a sufficient flexibility is ensured there.

In accordance with a preferred embodiment, the receiving element is designed to release a self-expanding stent system. In such stent systems, it is particularly advantageous if a repositioning of the stent is possible as a result of the fact that the stent can be reliably withdrawn into the receiving element In accordance with another preferred embodiment of the invention, the receiving element is designed to release a heart valve prosthesis that is implanted via a catheter and has a self-expanding basic frame, to which the actual heart valves are fastened. The heart valve prosthesis is particularly preferably designed to replace the natural aortic valve.

In the figures, functionally like or similarly acting elements are denoted in each case by like reference signs. The figures are schematic illustrations of the invention. They do not show specific parameters of the invention. The figures also merely reproduce typical embodiments of the invention and are not intended to limit the invention to the embodiments illustrated.

Figure 2:
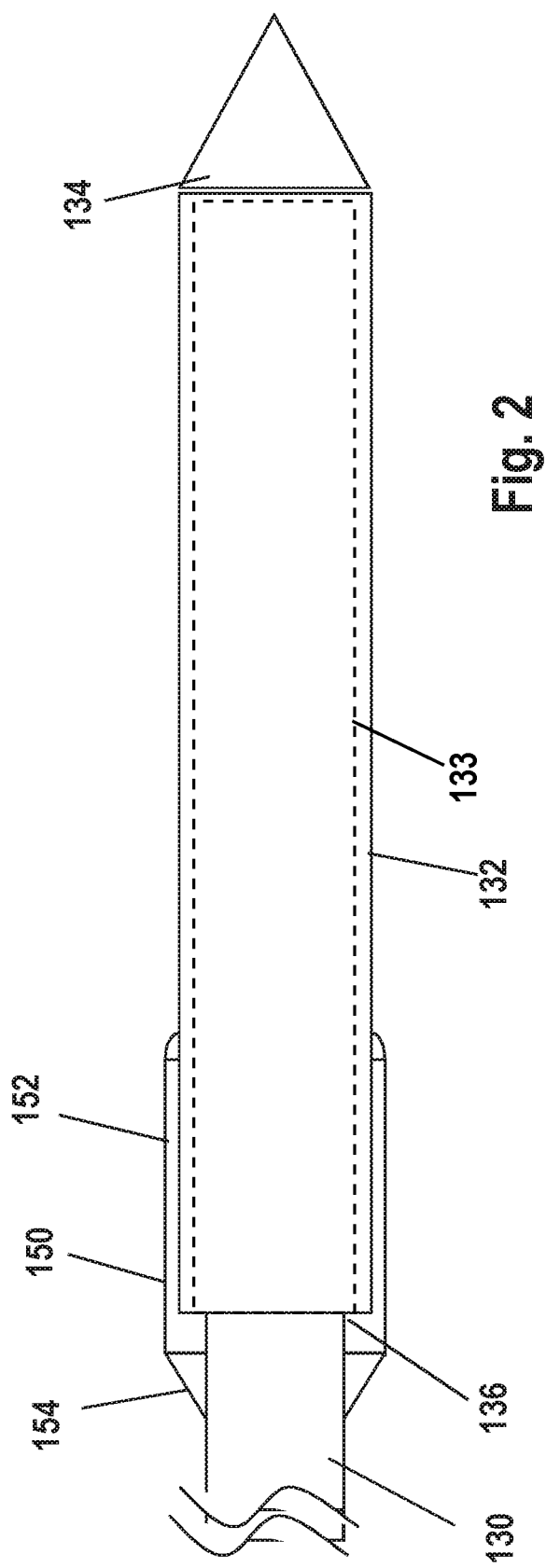
FIG. 2 schematically shows a detailed view at the distal end of the insertion device from FIG. 1.

FIG. 1 shows a view of an insertion device 100 in accordance with an exemplary embodiment of the invention in the form of a catheter with an outer shaft 130 and with a capsule as receiving element 132 for an implant 133. FIG. 2 shows a detailed view at the distal end of the insertion device 100 from FIG. 1.

The outer shaft 130 has a proximal end 102 with a grip 120, and a distal end 104, opposite said proximal end, with a tip 134. An outer shaft 130 extends between the proximal and distal end 102, 104 and has the receiving element 132, which is adjoined by the tip 134 at the distal end 104.

The insertion device 100 is used to introduce a medical implant 133 into a human and/or animal body having at least one outer shaft 130. The implant 133 may advantageously be a self-expanding stent system. Stent systems of this type have to be placed in a particularly accurate manner, and therefore the insertion device 100 is to ensure potential reliable repositioning. The implant 133 is transported to the site of use in a receiving element 132 connected to the outer shaft 130 and is released at that site. In the case of an incorrect positioning, the implant 133 released at the site of use is withdrawn again into the receiving element 132 and released again at a corrected position.

The outer shaft 130 generally forms the radially outer delimitation of the insertion device 100. In particular, one or more inner shafts can be arranged within the outer shaft 130, as are conventional in insertion systems of this type and as are known to a person skilled in the art.

The outer shaft 130 and the receiving element 132 are surrounded at a transition between the outer shaft 130 and receiving element 132 by a locally placed sleeve 150, which dampens at least some of the mechanical tensile and/or compressive stresses that are present in the curved state of the outer shaft 130. If these stresses were not damped, this could result in a deformation or a kinking at the transition between the outer shaft 130 and receiving element 132, which may negatively influence the function of the insertion element.

Whereas the outer shaft 130 usually has a considerable length, for example more than a meter, the sleeve 150 is short, for example a few centimeters, in particular 3 cm. Typical diameters of the outer shaft 130 and of the receiving element 132 are a few millimeters, for example 5 mm to 6 mm. The exact values are dependent on the specific design of the insertion system and can be adapted toward a specific design to achieve suitable dampening of stresses.

The sleeve 150 covers a proximal end 136 of the receiving element 132 in a first region 152 and a region 154 of the outer shaft 130 adjacent to the receiving element 132. Here, it is mechanically advantageous if 25% to 35% of the length of the sleeve 150 is arranged over the outer shaft 130 and if 75% to 65% is arranged over the receiving element 132.

The sleeve 150 is shrunk over the outer shaft 130, whereas it is shrunk to a lesser extent or is not shrunk over the receiving element 132, such that it is arranged in a floating manner over the receiving element 132. This ensures the movability of the receiving element 132. In an exemplary embodiment, a sleeve 150 with a length of 3 cm and an inner diameter (unshrunk) of 6.2 mm and an outer diameter of 6.4 mm is used. After shrinking, the inner diameter over the outer shaft 130 is 5.9 mm in this example and the outer diameter is 6.1 mm. The transition region between the outer shaft 130 and the receiving element 132 formed as a capsule is protected against kinking.

The sleeve 150 is advantageously formed as a shrink tubing made of PEEK

Figure 3:
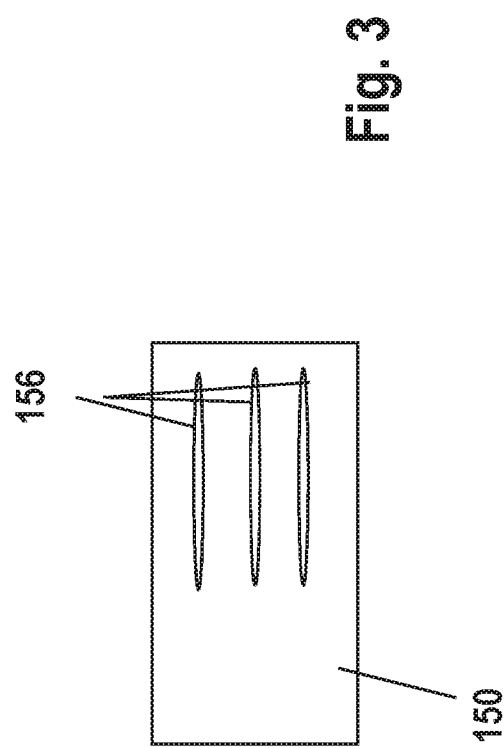
FIG. 3 schematically shows a detail of a sleeve in accordance with an exemplary embodiment of the invention.

FIG. 3 shows a detail of a sleeve 150 in accordance with an exemplary embodiment of the invention. The sleeve 150 is provided with slits 156 formed in the axial direction. The slits 156 are advantageously arranged at the transition between the outer shaft 130 and receiving element 132.

On the whole, the insertion device 100 according to the invention enables a simplification of the release process for a more accurate and more homogeneous positioning of an implant, and also the release and the withdrawal of the implant.

The insertion device 100 according to the invention is particularly advantageous in the case of the release of self-expanding stent systems, for the withdrawal of the protection of balloon-expanding stents or for the withdrawal of the protection of coated balloons. The design is easy to implement and is cost-effective.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein.

Therefore, it is the intent to cover all such modifications and alternate embodiments as may come within the true scope of this invention.

What is claimed is:

1. An insertion device for the insertion of a medical implant into a human and/or animal body, the insertion device comprising an outer shaft, which has a proximal end and a distal end opposite said proximal end, a receiving element, and a medical implant in the receiving element, the receiving element being connected at the distal end to the outer shaft, and a locally placed sleeve surrounding the outer shaft and the receiving element at a transition between the outer shaft and the receiving element to dampen mechanical tensile and/or compressive stresses, wherein the locally placed sleeve has at least one first and one second region, wherein the first region is arranged at the transition between the outer shaft and the receiving element and is shrunk, and the second region is arranged over the receiving element and is shrunk to a lesser extent than the first region.

2. The insertion device as claimed in claim 1, wherein the locally placed sleeve covers at least a proximal end of the receiving element.

3. The insertion device as claimed in claim 1, wherein the locally placed sleeve is formed from a material that can be contracted selectively from a state that is widened based on an inner diameter of the locally placed sleeve into a shrunken state.

4. The insertion device as claimed in claim 1, comprising slits in said locally placed sleeve.

5. The insertion device at least as claimed in claim 4, wherein the slits are arranged at the transition between the outer shaft and receiving element.

6. The insertion device as claimed in claim 1, wherein the locally placed sleeve is formed from a thermoplastic that contracts when heated.

7. The insertion device as claimed in claim 6, wherein the locally placed sleeve is formed from PEEK.

8. The insertion device as claimed in claim 1, wherein the medical implant comprises a self-expanding stent system.

9. The insertion device as claimed in claim 1, wherein the medical implant comprises a balloon expanding stent.

10. The insertion device as claimed in claim 1, wherein 25% to 35% of a length of the locally placed sleeve is arranged over the outer shaft and 75% to 65% of the length is arranged over the receiving element.

11. The insertion device as claimed in claim 10, wherein the locally placed sleeve is a few centimeters in length.

12. The insertion device as claimed in claim 11, wherein the outer shaft is more than a meter in length.

13. The insertion device as claimed in claim 1, wherein the receiving element is a capsule.

* * * * *